United States Patent [19]

Willner et al.

[11] 4,188,188

[45] Feb. 12, 1980

[54] HIGH DENSITY LIPOPROTEIN CHOLESTEROL ASSAY

[75] Inventors: Howard Willner, San Anselmo; Robert J. Kapteyn, Newport Beach, both of Calif.

[73] Assignee: Bio-Rad Laboratories, Inc., Richmond, Calif.

[21] Appl. No.: 945,982

[22] Filed: Sep. 27, 1978

[51] Int. Cl.[2] ..................... G01N 31/02; G01N 33/16; G01N 31/14

[52] U.S. Cl. .................................. 23/230 B; 252/408; 435/11

[58] Field of Search ...................... 23/230 B; 252/408; 424/183

[56] References Cited

U.S. PATENT DOCUMENTS

| | | | |
|---|---|---|---|
| 3,088,868 | 5/1963 | Windsor | 424/183 X |
| 3,247,063 | 4/1966 | Pulver | 424/183 |
| 3,870,790 | 3/1975 | Lowey | 424/183 |
| 3,975,162 | 8/1976 | Renn | 23/230 B X |
| 4,020,005 | 4/1977 | Lang | 252/408 X |
| 4,039,285 | 8/1977 | Teipel | 252/408 X |
| 4,045,176 | 8/1977 | Proksch | 23/230 B |
| 4,096,136 | 6/1978 | Ayers | 23/230 B |

OTHER PUBLICATIONS

W. T. Friedewald et al., Clin. Chem., 18(6), 499–502, (1972).

E. Cham, Clin. Chem., 22(11), 1812–1816, (1976).

Quanta–Zyme® Cholesterol Instruction Manual, Bio–Rad Laboratories, Bulletin 4219, May 1978.

HDL Cholesterol Instruction Manual, Bio–Rad Laboratories, 1978.

*Primary Examiner*—Sidney Marantz

*Attorney, Agent, or Firm*—Townsend and Townsend

[57] ABSTRACT

A reagent composition useful in assays for high density lipoprotein (HDL) cholesterol comprises heparin and a salt of a divalent metal cation such as $MnCl_2$ dispersed in an inert filler comprising a polysaccharide, a terminal interlocking linear glucose polymer and a vinylpyrrolidone. The cholesterol containing serum sample acts as the milieu of the reaction as well as the solvent for the reagent composition itself.

11 Claims, No Drawings

HIGH DENSITY LIPOPROTEIN CHOLESTEROL ASSAY

BACKGROUND OF THE INVENTION

Numerous studies have been published which point out the strong correlation which exists between levels of high density lipoprotein (HDL) cholesterol and reduced risk of clinically evident atherosclerosis. Thus the fractionation of cholesterol and the measurement of isolated fractions is of great diagnostic import.

Typically it is useful to separate out the high density lipoproteins from other serum components, most specifically from the low and very low density lipoproteins (LDL and VLDL), and then measure the HDL cholesterol by some form of assay, such as some condensation reaction, or enzyme assay. One method to effect such a separation utilizes the interaction between LDL and VLDL and polyanions and (Group II) metal ions, as exemplified by heparin and Ca. One such method known in the art is the heparin/$MnCl_2$ precipitation approach which utilizes heparin and $MnCl_2$ to precipitate out LDL and VLDL leaving the HDL in the serum solution. The precipitation approach for fractionation of cholesterol is described in Clin. Chem. 22/11, 1812–1816 (1976) and Clin. Chem. 18/6, 499–502 (1972).

In the practical application of these fractionation or separation procedures only minute quantities of the active ingredients, i.e., heparin and the divalent cation salt need be utilized. Accordingly, it is highly desirable to be able to premeasure these small quantities of active ingredients and to put them in a useful form in order to give precision and standardization to the assay procedure. Unfortunately, the required quantities are so small as to be virtually invisible to the naked eye. Thus, in addition to the difficulties inherent in measuring such small amounts of these key active ingredients, it is exceedingly difficult to move or handle the premeasured amounts without danger of some loss. For example, attempts to provide heparin and $MnCl_2$, premeasured and lyophilized, for use in the HDL cholesterol assay have produced unacceptable non-uniform results.

These disadvantages are overcome when the active ingredients for the separation of LDL and VLDL from HDL cholesterol are dispersed in an inert filler comprising a polysaccharide, a terminal interlocking linear glucose polymer and a vinylpyrrolidone. The filler not only adds bulk to the reagent mixture but does so without influencing the interaction of the active ingredients with the low and very low density lipoproteins. The presence of the filler prevents loss of heparin and divalent cation salt during lyophilization and/or other handling during which the active ingredients are put in forms useful for standardized testing, such as tablets.

Moreover, it has been found that when the reagent mixture of the present invention is employed in a HDL separation, the cholesterol containing serum sample itself acts as both the solvent for the reagent composition and as the milieu of the reaction.

SUMMARY OF THE INVENTION

In accordance with the present invention there is provided a novel reagent composition useful in assays for high density lipoprotein (HDL) cholesterol wherein low density lipoprotein (LDL) and very low density lipoprotein (VLDL) cholesterol fractions are precipitated leaving the HDL fraction in solution, the solution then being assayed for cholesterol. The novel reagent composition comprises heparin and a divalent cation salt, such as manganese chloride, dispersed in an inert filler, said filler comprising a polysaccharide, a terminal interlocking linear glucose polymer, and a vinylpyrrolidone polymer.

PREFERRED EMBODIMENT

Reagent compositions useful in the present invention are those comprising heparin and a divalent cation salt as active ingredients and a filler comprising a polysaccharide, preferably selected from the group consisting of sucrose, lactose, α-lactose, maltose, cellobiose and methylated disaccharides; a terminal interlocking linear glucose polymer, preferably having a molecular weight up to and including about M.W. 100,000, and a vinylpyrrolidone polymer, such as PVP K 10, preferably having a molecular wieght up to and including M.W. 100,000.

Typically, the filler will be present in amounts from 50–1000 and preferably 200–1000 parts by weight relative to the active ingredients. The heparin is typically present in weight ratios of from about 1:3 to 1:5 in relation to the divalent cation salt and preferably in a weight ratio of about 1:4.

The divalent cation salts useful in the present invention are those useful in the precipitation of lipoproteins and typically are those having the formula:

$$CX_2$$

wherein C is selected from the group consisting of Group IIA metals and manganese and X is a suitable anion for the metal. In the most preferred embodiment C is calcium or manganese and X is halogen, preferably chloride.

The specific description presented below utilizes the commercial cholesterol enzyme assay sold under the name Quanta-Zyme of Bio-Rad Laboratories, Inc. of Richmond, California, but other cholesterol assays such as chemiluminescent assays may also be used.

HDL Cholesterol Assay Procedure

1. To a polystyrene reaction tube containing 148 units heparin, 30 micromoles $MnCl_2$, 2 mg. dextran 15–20 M, 3 mg. α-lactose and 3 mg PVP K10 is added 500 ul of well mixed serum which has been collected after a 12–14 hour fast. Mix vigorously.
2. Place tube in refrigerator at 2–8° C. for 30 minutes.
3. Remove tube from refrigerator and centrifuge under refrigeration at 2–8° C. for 15 minutes at 3000 rpm.
4. Immediately transfer 25 ul of supernate to a clean, dry tube in which there is 3.0 ml of Enzyme-Substrate Reagent (ingredients listed in Quanta-Zyme Cholesterol Assay product insert). Mix.
5. Incubate the tube at 37° C. for 10 minutes.
6. Read and note spectrophotometer values to determine concentration of cholesterol in combination with appropriate blank and calibrator tubes.

What is claimed is:

1. A composition for use in a HDL cholesterol separation comprising heparin, a divalent cation salt having the formula: $CX_2$, wherein C is selected from the group consisting of Group IIA metals and manganese and X is a halogen, and an inert filler comprising a polysaccharide, a terminal interlocking linear glucose polymer and a vinylpyrrolidone polymer.

2. A composition as described in claim 1 wherein said polysaccharide is selected from the group consisting of lactose, α-lactose, sucrose, maltose, cellobiose and methylated disaccharides.

3. A composition as described in claim 1 or 2 wherein said terminal interlocking linear glucose polymer has a molecular weight up to about 100,000.

4. A composition as described in claim 1 or 2 wherein said vinyl pyrrolidone polymer has a molecular weight up to about 100,000.

5. A composition as described in claim 1 wherein said filler comprises α-lactose, dextran and PVP K 10.

6. A composition as described in claim 1, 2, or 5 wherein said filler is present in an amount equal to about 50–1000 parts by weight relative to the heparin and $MnCl_2$.

7. A composition as described in claim 6 wherein said heparin and said divalent cation salt are present in weight ratio of from about 1:3 to 1:5.

8. A composition as described in claim 7 wherein said heparin and said salt are present in a weight ratio of about 1:4.

9. A composition described in claim 1 wherein C is selected from the group consisting of calcium and manganese.

10. A composition described in claim 1 wherein said salt is selected from the group consisting of $MnCl_2$ and $CaCl_2$.

11. A high density lipoprotein cholesterol assay utilizing heparin/$MnCl_2$ precipitation, the improvement comprising adding to the serum sample to be assayed a reagent composition as described in claim 1, and assaying the resulting supernate for cholesterol.

* * * * *